United States Patent
Sato et al.

(10) Patent No.: US 11,400,033 B2
(45) Date of Patent: Aug. 2, 2022

(54) WATER-IN-OIL TYPE EMULSIFICATION COSMETIC

(71) Applicant: SHISEIDO COMPANY, LTD., Tokyo (JP)

(72) Inventors: Yukiko Sato, Yokohama (JP); Tomoko Ikeda, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/607,203

(22) PCT Filed: Apr. 25, 2018

(86) PCT No.: PCT/JP2018/016788
§ 371 (c)(1),
(2) Date: Oct. 22, 2019

(87) PCT Pub. No.: WO2018/199160
PCT Pub. Date: Nov. 1, 2018

(65) Prior Publication Data
US 2020/0038302 A1    Feb. 6, 2020

(30) Foreign Application Priority Data

Apr. 28, 2017    (JP) .............................. JP2017-089352

(51) Int. Cl.
*A61K 8/29*    (2006.01)
*A61K 8/02*    (2006.01)
*A61K 8/06*    (2006.01)
*A61K 8/92*    (2006.01)
*A61Q 1/02*    (2006.01)

(52) U.S. Cl.
CPC .............. *A61K 8/29* (2013.01); *A61K 8/0216* (2013.01); *A61K 8/064* (2013.01); *A61K 8/92* (2013.01); *A61Q 1/02* (2013.01)

(58) Field of Classification Search
None
See application file for complete search history.

(56) References Cited

U.S. PATENT DOCUMENTS

2012/0269748 A1* 10/2012 Tamura ................... C08L 83/14
424/59

FOREIGN PATENT DOCUMENTS

| JP | 2000063254 A | * | 2/2000 |
|----|----|----|----|
| JP | 2000-198716 | | 7/2000 |
| JP | 2004-168759 | | 6/2004 |
| JP | 2005-298482 | | 10/2005 |
| JP | 2005-298482 A | | 10/2005 |
| JP | 2010-132621 | | 6/2010 |
| JP | 2010-132621 A | | 6/2010 |
| JP | A 2010-132619 | | 6/2010 |
| JP | 2000-198716 A | | 7/2010 |
| JP | B 4629799 | | 2/2011 |
| JP | 2012-504570 | | 2/2012 |
| JP | 2012-504570 A | | 7/2012 |
| JP | 2013-121945 | | 6/2013 |
| JP | 2014-129297 | | 7/2014 |
| JP | 2017-048158 | | 3/2017 |

OTHER PUBLICATIONS

JP2012-504570A—Google English Translation (Year: 2012).*
JP2005-298482A—Google English Translation (Year: 2005).*
Scientific Committee on Consumer Safety (SCCS), "Opinion on cyclomethicone", 2010, pp. 1-103 (Year: 2010).*
Jp2000063254A, English translation of abstract (Year: 2000).*
PCT/JP2018/016788 International Search Report (ISR) and Written Opinion (WO), dated Jul. 24, 2018, 6 pages—English, 9 pages—Japanese.
JP 2017-089352, Office Action dated Dec. 11, 2020, 5 pages—Japanese, 6 pages—English.

* cited by examiner

*Primary Examiner* — Kyung S Chang
(74) *Attorney, Agent, or Firm* — Andrew F. Young; Nolte Lackenbach Siegel

(57) ABSTRACT

The purpose of the present invention is to provide a water-in-oil emulsified solid cosmetic having a relatively high internal-aqueous-phase proportion (about 40% or higher), the cosmetic being a makeup which has an excellent concealing effect and gives a natural finish and which is stable and has satisfactory applicability. The present invention relates to a solid cosmetic in water-in-oil emulsified type characterized by comprising (A) at least one fatty acid glyceryl ester selected from the group consisting of glyceryl isostearate, poly(2-glyceryl) diisostearate, and glyceryl oleate, (B) an aqueous component, (C) an oily component, and (D) a powdery component, the oily component (C) comprising a solid oil (C1) and an oil-soluble film former (C2) and the powdery component (D) comprising titanium dioxide (D1) having a primary-particle diameter of 0.05-0.5 μm in an amount of 10 mass % or more relative to the whole cosmetic preparation and further containing a pearl pigment (D2).

5 Claims, No Drawings

WATER-IN-OIL TYPE EMULSIFICATION COSMETIC

CROSS REFERENCE TO RELATED APPLICATIONS

This application relates to and claims priority as a § 371 national phase, from PCT/JP2018/016788 filed Apr. 25, 2018, the entire contents of which are incorporated herein by reference, which in turn claims priority from JP Ser. No.: 2017-089352 filed Apr. 28, 2017.

FIGURE SELECTED FOR PUBLICATION

N/A

TECHNICAL FIELD

The present invention relates to a water-in-oil emulsified makeup cosmetic. More particularly, the present invention relates to a water-in-oil emulsified solid cosmetic that spreads lightly and provides a natural finish, while providing a high concealing (covering) effect and (skin) correction effect.

BACKGROUND ART

It is known that a water-in-oil emulsified cosmetic may give a good refreshing feeling of use when the ratio obtained by dividing the amount of the internal aqueous phase component by the sum of all aqueous phase components and all oil phase components (i.e., internal aqueous phase ratio) increase, and whereas the emulsified cosmetic spreads lightly and provides an oily sensation (feel) when the internal aqueous phase ratio is low. It has been also found that a stable water-in-oil emulsified cosmetic was obtained by using glycerin monooleate or the like as a surfactant, regardless having a high internal aqueous phase ratio.

In Patent Document 1, it is stated that by comprising glycerin oleate and/or glycerin isostearate having a higher purity than a predetermined value and further including an isoparaffin having 20 or less carbon atoms, such as isohexadecane, in an amount of 30% by mass of the total amount of hydrocarbon oils or even higher, a water-in-oil emulsified cosmetic is stably obtained at an internal aqueous phase ratio not lower than 68%, and such a cosmetic is excellent in a full feeling and softness after being applied to the skin. However, a powder component is not contained in the cosmetic, so that the skin correction effect and the skin concealing effect are insufficient, and therefore, it is concerningly speculated that the cosmetic would become unstable even when a powder component is just simply added to the cosmetic.

Patent Document 2 describes a solid water-in-oil emulsified cosmetic in which glycerin monoisostearate is blended to provide a high internal aqueous phase ratio (50% or more). However, it is stated that the amount of the powder components blended in the cosmetic is just 10 to 30% by mass in total (paragraph [0023]), and the amount of pigment grade titanium dioxide therein is just 8% by mass at most, so that the concealing effect thereby is poor and unappreciable. In addition, whereas a sufficient concealing effect is obtainable when the amount of pigment grade titanium dioxide blended is simply increased in the system of Patent Document 2, the finish (of the makeup) looks whity and unnatural.

CITATION LIST

Patent Document

Patent Document 1: JP-B 4629799
Patent Document 2: JP-A 2010-132619

SUMMARY OF INVENTION

Technical Problem

The present invention has been made in view of the above technical aspects, and an object of the present invention is to provide a makeup cosmetic of which the concealing effect is excellent while providing a natural finish (appearance) with the quite stable and usable water-in-oil emulsified solid cosmetic having a relatively high internal aqueous phase ratio is (i.e., higher than about 40%).

Solution to Problem

The present inventors have studied diligently over and over in order to solve such problems and found that a makeup cosmetic, having the desired characteristics, was obtained by blending 10% by mass or more of titanium dioxide, having an average primary particle diameter in a predetermined range, and a pearl pigment in combination as a powder component and including an oil-soluble film-forming agent in an oily component, and completed the present invention.

Specifically, the present invention provides a water-in-oil emulsified solid cosmetic comprising (A) at least one fatty acid glyceryl ester selected from the group consisting of glyceryl isostearate, polyglyceryl-2 diisostearate, and glyceryl oleate; (B) an aqueous component; (C) an oily component; and (D) a powder component, wherein the (C) oily component comprises (C1) a solid oil component and (C2) an oil-soluble film-forming agent, and the (D) powder component comprises (D1) titanium dioxide having a primary particle diameter of 0.05 to 0.5 µm in an amount of 10% by mass or more based on a total amount of the cosmetic, and further comprises a (D2) pearl pigment.

Advantageous Effects of Invention

The water-in-oil emulsified solid cosmetic of the present invention is excellent in emulsification stability though having a relatively high internal aqueous phase ratio, exhibits an excellent correction effect with a high concealing effect, provides a natural finish, and in addition, spreads well and also gives a good fit feeling when applied to the skin.

DESCRIPTION OF EMBODIMENTS

The water-in-oil emulsified solid cosmetic (hereinafter also simply referred to as an "emulsified cosmetic") of the present invention contains, as an mandatory component, (A) at least one fatty acid glyceryl ester selected from the group consisting of glyceryl isostearate, polyglyceryl-2 diisostearate and glyceryl oleate (also referred to as an "Component A").

Glyceryl isostearate may be the glyceryl isostearate conventionally used for cosmetics and may be a mixture of glyceryl monoisostearate, glyceryl diisostearate, and/or glyceryl triisostearate but is preferably glyceryl isostearate comprising glyceryl monoisostearate. The purity (content) of glyceryl monoisostearate in glyceryl isostearate is not particularly limited but is preferably 40% by mass or more. As the commercial product, NIKKOL® MGIS (manufactured by Nikko Chemicals Co., Ltd.) and the like can be preferably used.

Glyceryl oleate may be glyceryl oleate conventionally used for cosmetics and may be a mixture of glyceryl monooleate, glyceryl dioleate, and/or glyceryl trioleate but is preferably glyceryl oleate comprising glyceryl monooleate. The purity (content) of glyceryl monooleate in glyceryl oleate is not particularly limited but is at least 40% by mass or more, preferably 60% by mass or more, and more preferably 85% by mass or more.

Polyglyceryl-2 diisostearate is the diester of isostearic acid and diglycerin. In the present invention, commercial products may be used, and, for example, EMALEX DISG-2 (Nihon Emulsion Co., Ltd.) can be illustrated.

The fatty acid glyceryl ester (Component A) in the emulsified cosmetic of the present invention may be any one of glyceryl isostearate, polyglyceryl-2 diisostearate, or glyceryl oleate, or two or more may be used in combination. Among them, glyceryl monoisostearate, glyceryl monooleate, or polyglyceryl-2 diisostearate is preferably used.

The amount of the fatty acid glyceryl ester (Component A) blended in the emulsified cosmetic of the present invention is usually within the range of 0.1 to 10% by mass, preferably 1.0 to 3.0% by mass, and more preferably 1.0 to 2.5% by mass based on the total amount of the cosmetic. When the amount blended is less than 0.1% by mass, the stability of the emulsion may be impaired. When the fatty acid glyceryl ester (Component A) is blended in an amount exceeding 10% by mass, the usability such as remaining refreshingness may be poor.

(B) Aqueous Component

The aqueous component (also referred to as a "Component B") blended in the emulsified cosmetic of the present invention comprises water, and an aqueous component that can usually be blended in cosmetics and the like. Examples thereof include, but are not limited to, moisturizers, water-soluble polymers, water-soluble agents, sequestering agents, and antioxidants.

Examples of the moisturizers include 1,3-butylene glycol, polyethylene glycol, propylene glycol, dipropylene glycol, hexylene glycol, glycerin, diglycerin, xylitol, maltitol, maltose, and D-mannite.

Examples of the water-soluble polymers include plant-based polymers such as gum arabic, carrageenan, pectin, agar, quince seed (*Cydonia oblonga*), starch, and algae colloids (brown algae extracts), microorganism-based polymers such as dextran and pullulan, animal-based polymers such as collagen, casein, and gelatin, starch-based polymers such as carboxymethyl starch and methylhydroxypropyl starch, alginic acid-based polymers such as sodium alginate, vinyl-based polymers such as carboxyvinyl polymers (CARBOPOL® and the like), polyoxyethylene-based polymers, polyoxyethylene polyoxypropylene copolymer-based polymers, acrylic polymers such as sodium polyacrylate, polyacrylamide, and polymethyl methacrylate, and inorganic water-soluble polymers such as bentonite, aluminum magnesium silicate, and LAPONITE®.

Examples of the water-soluble agents include vitamins such as vitamin A, retinol, retinol palmitate, inositol, pyridoxine hydrochloride, benzyl nicotinate, nicotinic acid amide, dl-α-tocopherol nicotinate, magnesium ascorbyl phosphate, ascorbic acid 2-glucoside, vitamin D2 (ergocalciferol), dl-α-tocopherol 2-L ascorbic acid phosphoric acid diester potassium salt, dl-α-tocopherol, dl-α-tocopherol acetate, pantothenic acid, and biotin, anti-inflammatory agents such as allantoin and azulene, skin-whitening agents such as arbutin, astringents such as zinc oxide and tannic acid, sulfur, lysozyme chloride, and γ-oryzanol.

Examples of the sequestering agents include sodium edetate, sodium metaphosphate, and phosphoric acid.

Examples of the antioxidants include ascorbic acid, α-tocopherol, dibutylhydroxytoluene, and butylhydroxyanisole.

The amount of the aqueous component (Component B) blended in the emulsified cosmetic of the present invention is usually within the range of 20 to 70% by mass, preferably 30 to 60% by mass, and more preferably 30 to 50% by mass based on the total amount of the cosmetic. When the amount blended is less than 20% by mass, the refreshing good feel may be impaired. When the aqueous component (Component B) is blended in an amount exceeding 70% by mass, there are cases where emulsification cannot be stably performed.

The (C) oily component (also referred to as a "Component C") in the present invention contains (C1) a solid oil component and (C2) an oil-soluble film-forming agent as essential components.

As the (C1) solid oil component, solid oils and fats such as cacao butter, coconut oil, horse oil, hydrogenated coconut oil, palm oil, beef tallow, mutton tallow, and hydrogenated castor oil, hydrocarbons such as polyethylene wax, paraffin waxes (straight chain hydrocarbons), microcrystalline waxes (branched saturated hydrocarbons), ceresin wax, Japan wax, montan wax, and Fischer-Tropsch waxes, waxes such as beeswax, lanolin, carnauba wax, candelilla wax, rice bran wax (rice wax), spermaceti wax, jojoba oil, bran wax, kapok wax, bayberry wax, shellac wax, sugarcane wax, lanolin fatty acid isopropyl, hexyl laurate, reduced lanolin, hard lanolin, POE lanolin alcohol ethers, POE lanolin alcohol acetates, POE cholesterol ether, lanolin fatty acid polyethylene glycols, and POE hydrogenated lanolin alcohol ethers, higher fatty acids such as myristic acid, palmitic acid, stearic acid, and behenic acid, higher alcohols such as cetyl alcohol, stearyl alcohol, behenyl alcohol, myristyl alcohol, and cetostearyl alcohol, and the like can be illustrated.

Among the above solid oil components, waxes having a melting point of 70° C. or higher or 75° C. or higher are preferred, and among them, waxes having a melting point of 95° C. or lower or 90° C. or lower are preferred. Examples of such waxes include rice bran wax and polyethylene wax.

The (C2) oil-soluble film-forming agent is not particularly limited as long as it is one usually used for cosmetics. Specific examples include trimethylsiloxysilicic acid, dimethylaminomethacrylate quaternary salts, vinylpyrrolidone-N,N-dimethyl-ethylantinioethyl methacrylate salt copolymers, silicone/polyether-based polyurethane resins, (methacryloyloxyethylcarboxybetaine/methacrylic alkyl) copolymers, dextrin, (vinylpyrrolidone/VA) copolymers, alkyl acrylate copolymer ammonium, polyvinyl alcohol, polyethyl acrylate, (alkyl acrylate/octylacrylamide) copolymers, (acrylate/propyl trimethicone methacrylate) copolymers, polyvinyl acetate, (acrylate/dimethicone) copolymers, 3-[tris(trimethylsiloxy)silyl]propyl carbamate pullulan, polyether-grafted acrylic silicones, and fluoro-modified silicone resins. Among them, trimethylsiloxysilicic acid, (acrylate/dimethicone) copolymers, and 3-[tris(trimethylsiloxy)silyl]propyl carbamate pullulan are preferred.

The (C) oily component in the emulsified cosmetic of the present invention may optionally comprise an oily component that can usually be blended in cosmetics and the like, in addition to the (C1) solid oil component and the (C2) oil-soluble film-forming agent. Examples of the oily component that can be optionally blended include, but are not limited to liquid oil components, (oil-soluble) ultraviolet absorbing agents, oily thickening agents, oily agents, and perfumes.

The liquid oil components include silicone oils and hydrocarbon oils, and the emulsified cosmetic of the present invention preferably comprises a silicone oil. Examples of the silicone oils include chain silicone oils such as dimethylpolysiloxane, methylphenylpolysiloxane, methylhydrogenpolysiloxane, polyether-modified silicones, and phenyl-modified silicones, and cyclic silicone oils (cyclomethicones) such as octamethylcyclotetrasiloxane, decamethylcyclopentasiloxane, and dodecamethylcyclohexasiloxane.

The hydrocarbon oils include polar oils and nonpolar oils. Examples of the polar oils include ester oils such as cetyl octanoate, hexyl laurate, isopropyl myristate, octyl palmitate, isocetyl stearate, isopropyl isostearate, octyl isopalmitate, isodecyl oleate, 2-ethylhexyl succinate, and diethyl sebacate. Examples of the nonpolar oils include liquid paraffins, squalane, squalene, paraffins, isoparaffins, isododecane, and isohexadecane.

Examples of the ultraviolet absorbing agents include benzoic acid-based ultraviolet absorbing agents such as para-aminobenzoic acid, anthranilic acid-based ultraviolet absorbing agents such as methyl anthranilate, salicylic acid-based ultraviolet absorbing agents such as octyl salicylate and phenyl salicylate, cinnamic acid-based ultraviolet absorbing agents such as isopropyl para-methoxycinnamate, octyl para-methoxycinnamate (ethylhexyl methoxycinnamate), and glyceryl di-para-methoxycinnamate mono-2-ethylhexanoate, benzophenone-based ultraviolet absorbing agents such as 2,4-dihydroxybenzophenone, 2-hydroxy-4-methoxybenzophenone, and 2-hydroxy-4-methoxybenzophenone-5-sulfonic acid, urocanic acid, 2-(2'-hydroxy-5'-methylphenyl)benzotriazole, and 4-tert-butyl-4'-methoxybenzoylmethane.

The amount of the oily component (Component C) blended in the emulsified cosmetic of the present invention is usually within the range of 10 to 50% by mass, preferably 15 to 40% by mass, and more preferably 15 to 30% by mass based on the total amount of the cosmetic. The amount of the blended (C1) solid oil component contained in the oily component is usually 0.1 to 10% by mass, preferably 0.1 to 5% by mass, and more preferably 1 to 3% by mass based on the total amount of the cosmetic, and the amount of the (C2) oil-soluble film-forming agent blended is usually within the range of 0.1 to 20% by mass, preferably 1 to 15% by mass, and more preferably 5 to 10% by mass based on the total amount of the cosmetic.

The (D) powder component in the emulsified cosmetic of the present invention contains (D1) titanium dioxide having a primary particle diameter of 0.05 to 0.5 μm and (D2) a pearl pigment as essential components.

The (D1) titanium dioxide used in the present invention is titanium dioxide whose average primary particle diameter is 0.05 to 0.5 μm, preferably 100 to 400 nm (hereinafter also referred to as "pigment grade titanium dioxide").

The average primary particle diameter herein means the diameter of primary particles measured by a generally used method for a powder such as titanium dioxide and specifically means a value obtained as the arithmetic mean of the major axes and minor axes of particles measured from a transmission electron micrograph, a laser scattering-diffraction method, or the like. The shape of the pigment grade titanium dioxide is a spherical shape, an elliptical shape, a crushed shape, or the like and is not particularly limited.

The (D1) pigment grade titanium dioxide used in the present invention is preferably pigment grade titanium dioxide subjected to surface hydrophobization treatment. Examples of the method of the surface treatment include silicone treatment with methylhydrogenpolysiloxane, methylpolysiloxane, or the like; fluorine treatment with a perfluoroalkyl phosphate, a perfluoroalcohol, or the like; amino acid treatment with N-acylglutamic acid or the like; and in addition, lecithin treatment; metallic soap treatment; fatty acid treatment; and alkyl phosphate treatment.

The amount of the (D1) pigment grade titanium dioxide blended in the emulsified cosmetic of the present invention is usually within the range of 10 to 40% by mass, preferably 12 to 30% by mass, and more preferably 15 to 25% by mass based on the total amount of the cosmetic. When the amount blended is less than 10% by mass, a sufficient concealing effect may not be obtained. When the (D1) pigment grade titanium dioxide is blended in an amount exceeding 40% by mass, the finish may be white and unnatural.

The (D2) pearl pigment blended in the emulsified cosmetic of the present invention can be selected from those that can usually be blended in cosmetics, for example, titanium dioxide-coated mica (titanated mica), titanium dioxide-coated bismuth oxychloride, titanium dioxide-coated talc, colored titanium dioxide-coated mica, bismuth oxychloride, and argentine. Among them, pearl pigments obtained by coating the surface of a base material comprising flaky mica with a titanium dioxide layer are preferred.

The amount of the (D2) pearl pigment blended in the emulsified cosmetic of the present invention is usually within the range of 0.1 to 20% by mass, preferably 1 to 10% by mass, and more preferably 2 to 5% by mass based on the total amount of the cosmetic. When the amount blended is less than 0.1% by mass, the effect of pearl pigment blending may not be obtained. When the (D2) pearl pigment is blended in an amount exceeding 20% by mass, the finish may be white and unnatural.

In the emulsified cosmetic of the present invention, it is particularly preferred to blend, as the (D2) pearl pigment, titanated mica having a gold interference color, titanated mica having a red to yellow interference color, and titanated mica having a blue to green interference color in combination, from the viewpoint of a natural finish. For example, it is preferred to blend, in combination, pearl pigments obtained by coating the surface of a base material comprising flaky mica with a titanium dioxide layer, being a pearl pigment having a titanium dioxide layer having a film thickness of 80 to 100 nm (gold interference color), a pearl pigment having a titanium dioxide layer having a film thickness of 100 to 120 nm (for example, 101 to 120 nm) (red to yellow interference color), and a pearl pigment having a titanium dioxide layer having a film thickness of 120 to 150 nm (for example, 121 to 150 nm) (blue to green interference color).

The mixing ratio when titanated mica having a gold interference color, titanated mica having a red to yellow interference color, and titanated mica having a blue to green interference color are blended is not particularly limited but is preferably, for example, 1:1:1, 2:1:1, 2:2:1, 2:1:2, or the like.

The (D) powder component in the emulsified cosmetic of the present invention may comprise other powder components in addition to the (D1) pigment grade titanium dioxide and the (D2) pearl pigment in a range that does not inhibit the effects of the present invention.

Examples of other powder components include inorganic powders (for example, talc, kaolin, sericite, muscovite, synthetic mica, phlogopite, lepidolite, biotite, lithia mica, vermiculite, magnesium carbonate, calcium carbonate, diatomaceous earth, magnesium silicate, calcium silicate, aluminum silicate, barium silicate, strontium silicate, metal tungstates, silica, hydroxyapatite, zeolite, boron nitride, and ceramic powders); organic powders (for example, polyamide resin powders (nylon powders), polyethylene powders, polymethyl methacrylate powders, polystyrene powders, styrene-acrylic acid copolymer resin powders, benzoguanamine resin powders, polyethylene tetrafluoride powders, and cellulose powders); inorganic white pigments (for example, zinc oxide); inorganic red pigments (for example, iron titanate); inorganic purple pigments (for example, mango violet and cobalt violet); inorganic green pigments (for example, chromium oxide, chromium hydroxide, and cobalt titanate); inorganic blue pigments (for example, ultramarine blue and iron blue); metal powder pigments (for example, aluminum powders and copper powders); organic pigments such as zirconium, barium, or aluminum lakes (for example, Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404, Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1); and natural dyes (for example, chlorophyll and β-carotene).

The emulsified cosmetic of the present invention is a water-in-oil emulsified solid cosmetic comprising the above essential components (A) to (D), and preferably a solid cosmetic in which the ratio obtained by dividing the amount of the internal aqueous phase component by the sum of all aqueous phase components and all oil phase components (internal aqueous phase ratio) is 35% or more, more preferably 40% or more.

The "solid cosmetic" herein means a solid cosmetic having no fluidity in the normal temperature range in which cosmetics are used (0° C. to 40 ° C.). For example, the solid cosmetic is preferably a base in which the hardness γ represented by the following formula, measured using a known measuring apparatus such as a rheometer is 30 or more.

$$\gamma = (G*L)/(l*a) \ (dyn/cm^2)$$

wherein G: measured stress (gr)*980 dyn, L: the thickness (mm) of the sample, 1: compression distance (mm), a: the cross-sectional area (cm$^2$) of the needle (Measurement Conditions)

Load weight: 200 g, Needle diameter: 5.6 φ, Penetration rate: 2 cm/min, Penetration distance: 1 mm, Measurement temperature: 37° C.

The emulsified cosmetic of the present invention can be produced according to a production method widely used in the cosmetic field. For example, the emulsified cosmetic of the present invention can be produced by appropriately heating and mixing oil phase components, and stirring aqueous phase components separately prepared, for emulsification.

The water-in-oil emulsified solid cosmetic of the present invention can be widely applied to makeup cosmetics to be applied to the skin, the eyebrows, the eyelashes, the lips, and the like and is particularly suitable for use, for example, as foundations, cosmetic bases, eye shadows, eyeliners, and mascaras, and especially as foundations or cosmetic bases.

For the cosmetic of the present invention, the aspect of the container containing cosmetics is not limited. For example, in addition to a form in which the cosmetic of the present invention is filled into a container and solidified like conventional solid cosmetics, it is also possible to impregnate an impregnation body with the cosmetic of the present invention in a state of being fluidized in a production process, and contain the impregnated body in a compact container having airtightness. Examples of the impregnation body include nonwoven fabrics comprising single or mixed materials of resins, pulp, cotton and the like, resin-treated fibrous bodies, foams such as sponges, and porous bodies having continuous pores. As the material of the impregnation body, NBR (acrylonitrile butadiene rubber), SBR (styrene butadiene rubber), NR (natural rubber), urethanes, nylons, polyolefins, polyesters, EVA (ethylene vinyl acetate), PVA (polyvinyl alcohol), silicone rubber, elastomers, and the like are illustrated, but it is not limited to these materials.

EXAMPLES

The present invention will be described in more detail below by giving Examples, but the present invention is not limited by these Examples. The amounts blended are expressed in % by mass unless otherwise noted.

Water-in-oil emulsified cosmetics (foundations) were prepared with the formulations enumerated in the following Table 1 and Table 2. The "concealing effect", "the lightness of spread", and "the naturalness of the finish" for the cosmetic of each example were evaluated by the following method.

An actual use test was carried out for the cosmetic of each example by 10 expert panelists. Specifically, the foundation of each example was applied to the face of each panelist and evaluated according to the following criteria.

<Evaluation Criteria>

A+: 9 or more out of 10 panelists evaluated the cosmetic as excellent

A−: 7 to 8 out of 10 panelists evaluated the cosmetic as excellent

B: 5 to 6 out of 10 panelists evaluated the cosmetic as excellent

C: less than 5 out of 10 panelists evaluated the cosmetic as excellent

TABLE 1

|  | Example 1 | Example 2 | Example 3 | Example 4 | Example 5 | Example 6 | Example 7 | Example 8 |
|---|---|---|---|---|---|---|---|---|
| Glyceryl monoisostearate *1) | 1.5 | 1.5 | 2 | 1 | 2.5 | — | — | 1.5 |
| Polyglyceryl-2 diisostearate-2 | — | — | — | — | — | 2.0 | — | — |
| Glyceryl oleate | — | — | — | — | — | — | 1.5 | — |
| Polyether-modified silicone | 0.5 | — | 0.1 | 0.5 | 0.1 | 0.5 | 0.5 | 0.5 |
| Isohexadecane | 2 | — | 10 | 2 | 2 | 2 | 2 | 2 |
| Cyclomethicone | 10 | 10 | 15 | 20 | 10 | 10 | 10 | 10 |
| Phenyl-modified silicone | 1 | 2 | 2 | 2 | 2 | 1 | 1 | — |
| Ethylhexyl methoxycinnamate | — | 2 | 3 | 3 | 3 | — | — | — |

TABLE 1-continued

|  | Example 1 | Example 2 | Example 3 | Example 4 | Example 5 | Example 6 | Example 7 | Example 8 |
|---|---|---|---|---|---|---|---|---|
| Rice bran wax | 3 | — | 3 | 5 | 5 | 3 | 3 | — |
| Polyethylene wax | — | 3 | 1 | — | — | — | — | — |
| Stearic acid | — | — | — | — | — | — | — | 3 |
| Trimethylsiloxysilicic acid | 6 | 10 | — | — | — | 6 | 6 | 6 |
| (Acrylate/dimethicone) copolymer | — | — | 3 | — | 6 | — | — | — |
| 3-[tris(trimethylsiloxy)silyl]propyl carbamate pullulan | — | — | — | 3 | — | — | — | — |
| Hydrophobized titanium dioxide | 20 | 10 | 15 | 20 | 25 | 20 | 20 | 20 |
| Hydrophobized yellow iron oxide | 4 | 2 | 4 | 4 | 4 | 4 | 4 | 4 |
| Hydrophobized red iron oxide | 2 | 1 | 2 | 2 | 2 | 2 | 2 | 2 |
| Hydrophobized black iron oxide | 0.1 | 0.05 | 0.1 | 0.1 | 0.1 | 0.1 | 0.1 | 0.1 |
| Polymethyl methacrylate | — | 2 | 2 | — | — | — | — | — |
| Pearl pigment A *2) | 1 | 2 | 1 | 2 | 1 | 1 | 1 | 1 |
| Pearl pigment B *3) | 1 | 1 | 0.5 | 2 | 1 | 1 | 1 | 1 |
| Pearl pigment C *4) | 1 | 2 | 0.5 | 2 | 1 | 1 | 1 | 1 |
| Dipropylene glycol | 5 | 5 | 5 | 5 | 5 | 5 | 5 | 5 |
| Sodium chloride | 1 | 1 | 1 | 1 | 1 | 1 | 1 | 1 |
| Glycerin | 5 | 5 | 5 | 5 | 5 | 5 | 5 | 5 |
| Water | Balance | Balance | Balance | Balance | Balance | Balance | Balance | Balance |
| Total | 100 | 100 | 100 | 100 | 100 | 100 | 100 | 100 |
| Concealing effect | A+ | A− | A− | A+ | A+ | A+ | A+ | B |
| Lightness of spreading | A+ | A+ | A+ | A− | A− | A+ | A+ | A |
| Naturalness of finish | A+ | A+ | A+ | A+ | A− | A+ | A+ | A |

*1) NIKKOL ® MGIS (manufactured by Nikko Chemicals Co., Ltd.)
*2) A pearl pigment obtained by using flaky mica as a substrate and coating its surface with a titanium dioxide layer (film thickness of titanium dioxide layer: 80 to 100 nm)
*3) A pearl pigment obtained by using flaky mica as a substrate and coating its surface with a titanium dioxide layer (film thickness of titanium dioxide layer: 100 to 120 nm)
*4) A pearl pigment obtained by using flaky mica as a substrate and coating its surface with a titanium dioxide layer (film thickness of titanium dioxide layer: 120 to 150 nm)

TABLE 2

|  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|
| Glyceryl monoisostearate *1) | — | 2 | 1.5 | 2 | 1 | 0.5 | 0.5 |
| Polyether-modified silicone | 2 | 0.5 | 0.5 | 0.5 | 1 | 1 | 1 |
| Isohexadecane | 2 | 2 | 2 | 2 | 2 | 2 | 2 |
| Cyclomethicone | 10 | 10 | 10 | 10 | 10 | 10 | 10 |
| Rice bran wax | 3 | — | 3 | — | — | 3 | 3 |
| Polyethylene wax | — | — | — | 5 | — | — | — |
| Stearic acid |  |  |  |  |  |  |  |
| Trimethylsiloxysilicic acid | 6 | 6 | 6 | 6 | — | — | — |
| (Acrylate/dimethicone) copolymer | — | — | — | — | 6 | — | — |
| Hydrophobized titanium dioxide | 20 | 10 | 5 | 20 | 20 | 20 | 20 |
| Hydrophobized yellow iron oxide | 4 | 4 | 1 | 4 | 4 | 4 | 4 |
| Hydrophobized red iron oxide | 2 | 2 | 0.5 | 2 | 2 | 2 | 2 |
| Hydrophobized black iron oxide | 0.1 | 0.1 | 0.02 | 0.1 | 0.1 | 0.1 | 0.1 |
| Pearl pigment A *2) | 1 | 1 | — | — | 1 | 1 | — |
| Pearl pigment B *3) | 1 | 1 | — | — | 1 | 1 | — |
| Pearl pigment C *4) | 1 | 1 | — | — | 1 | 1 | — |
| Dipropylene glycol | 5 | 5 | 5 | 5 | 5 | 5 | 5 |
| Sodium chloride | 1 | 1 | 1 | 1 | 1 | 1 | 1 |
| Glycerin | 5 | 5 | 5 | 5 | 5 | 5 | 5 |
| Water | Balance | Balance | Balance | Balance | Balance | Balance | Balance |
| Total | 100 | 100 | 100 | 100 | 100 | 100 | 100 |
| Concealing effect | C | C | C | A | C | C | C |
| Lightness of spreading | A | A | A | B | A | B | B |
| Naturalness of finish | B | A | C | C | B | B | C |

*1) NIKKOL ® MGIS (manufactured by Nikko Chemicals Co., Ltd.)
*2) A pearl pigment obtained by using flaky mica as a substrate and coating its surface with a titanium dioxide layer (film thickness of titanium dioxide layer: 80 to 100 nm)
*3) A pearl pigment obtained by using flaky mica as a substrate and coating its surface with a titanium dioxide layer (film thickness of titanium dioxide layer: 100 to 120 nm)
*4) A pearl pigment obtained by using flaky mica as a substrate and coating its surface with a titanium dioxide layer (film thickness of titanium dioxide layer: 120 to 150 nm)

As shown in Table 1, for the cosmetics according to the present invention (Examples 1 to 8), satisfactory results were obtained as for all evaluation items including the concealing effect, the lightness of spreading, and the naturalness of the finish. Among them, for Example 8 comprising no wax having a melting point of 70° C. or more as (C1) a solid oil component, the concealing effect decreased to some extent, but Example 8 was at an unproblematic level as a product.

On the other hand, according to the results shown in Table 2, for Comparative Example 1 comprising no (A) fatty acid glyceryl ester and Comparative Examples 2 and 5 comprising no (C1) solid oil component, a sufficient concealing effect was not obtained. For Comparative Examples 3, 4 and 7 in which (D2) a pearl pigment was not blended, the finish was unnatural. For Comparative Example 3 in which the amount of pigment grade titanium dioxide blended was less than 10% by mass, the concealing effect was also poor. Also, for Comparative Examples 6 and 7 comprising no (C2) oil-soluble film-forming agent, a sufficient concealing effect was not obtained, and the finish was also unnatural.

Another formulation example of the present invention will be provided below. The cosmetic base with this formulation also had characteristics equivalent to those of the above Examples 1 to 7.

Formulation Example 1: Cosmetic Base

| | | |
|---|---|---|
| 1. | glyceryl monoisostearate*1) | 1.5 |
| 2. | polyether-modified silicone | 0.2 |
| 3. | isododecane | 5 |
| 4. | cetyl ethylhexanoate | 5 |
| 5. | ethylhexyl methoxycinnamate | 5 |
| 6. | cyclomethicone | 10 |
| 7. | rice bran wax | 3 |
| 8. | trimethylsiloxysilicic acid | 5 |
| 9. | hydrophobized titanium dioxide | 10 |
| 10. | hydrophobized red iron oxide | 0.01 |
| 11. | hydrophobized fine particle titanium dioxide | 3 |
| 12. | polymethyl methacrylate | 10 |
| 13. | pearl pigment A *2) | 0.1 |
| 14. | pearl pigment B *3) | 0.1 |
| 15. | pearl pigment C *4) | 0.1 |
| 16. | dipropylene glycol | 5 |
| 17. | glycerin | 1 |
| 18. | water | remainder |

*1) NIKKOLO ® MGIS (manufactured by Nikko Chemicals Co., Ltd.)
*2) A pearl pigment obtained by using flaky mica as a substrate and coating its surface with a titanium dioxide layer (film thickness of titanium dioxide layer: 80 to 100 nm)
*3) A pearl pigment obtained by using flaky mica as a substrate and coating its surface with a titanium dioxide layer (film thickness of titanium dioxide layer: 100 to 120 nm)
*4) A pearl pigment obtained by using flaky mica as a substrate and coating its surface with a titanium dioxide layer (film thickness of titanium dioxide layer: 120 to 150 nm)

Production Method:

The above 1 to 8 were uniformly heated and mixed (oil phase portion), 9 to 15 (powder portion) were added thereto and dispersed, and further, heated and melted 16 to 18 (aqueous phase portion) were mixed to obtain a cosmetic base.

The invention claimed is:

1. A water-in-oil emulsified solid cosmetic, comprising:
   (A) at least one fatty acid glyceryl ester selected from a group consisting of glyceryl isostearate, polyglyceryl-2 diisostearate and glyceryl oleate;
   (B) an aqueous component;
   (C) an oily component; and
   (D) a powder component,
wherein
   said (C) oily component comprises:
      (C1) a solid oil component and (C2) an oil-soluble film-forming agent, wherein said (C2) oil-soluble film-forming agent is at least one selected from the group consisting of trimethylsiloxysilicic acid, silicone/polyether-based polyurethane resins, acrylate/propyl trimethicone methacrylate copolymers, acrylate/dimethicone copolymers, 3-[tris(trimethylsiloxy)silyl] propyl carbamate pullulan, polyether-grafted acrylic silicones, and fluoro-modified silicone resins; and
wherein
   said (D) powder component comprises:
      (D1) a titanium dioxide having a primary particle diameter of 0.05 to 0.5 µm in an amount of 15 to 40% by mass based on a total amount of said cosmetic, and (D2) a pearl pigment.

2. The cosmetic according to claim 1, wherein said (D2) pearl pigment comprises:
   a pearl pigment having a base material and a coating, wherein said base material is a flaky mica and said coating is a titanium dioxide layer.

3. The cosmetic according to claim 2, wherein said pearl pigment having said base material and said coating comprises at least one of:
   a pearl pigment having a titanium dioxide layer having a thickness of 80 to 100 nm,
   a pearl pigment having a titanium dioxide layer having a thickness of 101 to 120 nm, and
   a pearl pigment having a titanium dioxide layer having a thickness of 121 to 150 nm.

4. The cosmetic according to claim 1, wherein said (C1) solid oil component comprises:
   a wax having a melting point at least 70° C.

5. The cosmetic according to claim 1 wherein the cosmetic is a makeup cosmetic.

* * * * *